United States Patent
Le Bourdelles et al.

(10) Patent No.: US 7,157,249 B2
(45) Date of Patent: Jan. 2, 2007

(54) DELTA SUBUNIT OF HUMAN GABAA RECEPTOR

(75) Inventors: Beatrice Le Bourdelles, Sawbridgeworth (GB); Paul John Whiting, Stansted Mountfitchet (GB)

(73) Assignee: Merck Sharp & Dohme Ltd., Hoddesdon (DE)

( * ) Notice: Subject to any disclaimer, the term of this patent is extended or adjusted under 35 U.S.C. 154(b) by 691 days.

(21) Appl. No.: 10/211,673

(22) Filed: Aug. 2, 2002

(65) Prior Publication Data

US 2003/0013158 A1    Jan. 16, 2003

Related U.S. Application Data

(62) Division of application No. 08/809,802, filed as application No. PCT/GB95/02323 on Sep. 29, 1995, now Pat. No. 6,455,276.

(30) Foreign Application Priority Data

Oct. 1, 1994   (GB)  ................................. 9420010.2

(51) Int. Cl.
  *C07H 21/04*  (2006.01)
  *C12N 15/63*  (2006.01)
  *C12N 5/16*   (2006.01)
  *C07K 14/705* (2006.01)

(52) U.S. Cl. .................. 435/69.1; 435/320.1; 435/325; 514/12; 536/23.5

(58) Field of Classification Search .................... None
See application file for complete search history.

(56) References Cited

U.S. PATENT DOCUMENTS 4,513,135 A * 4/1985 Wong et al. ................. 544/120

OTHER PUBLICATIONS

Luirk et al., *Eur. J. Pharmacol.*, vol. 290, pp. 175-181, 1995. (Abstract Only).*

* cited by examiner

*Primary Examiner*—Janet L. Andres
*Assistant Examiner*—Stephen Gucker
(74) *Attorney, Agent, or Firm*—Heidi M. Struse; Jack Tribble

(57) ABSTRACT

The present invention relates to the cloning of novel cDNA sequences encoding the $\alpha_4$ and $\delta$ receptor subunits of the human $GABA_A$ receptor; to stably co-transfected eukaryotic cell lines capable of expressing a human $GABA_A$ receptor, which receptor comprises at least one of the novel $\alpha_4$ and $\delta$ receptor subunits; and to the use of such cell lines in screening for and designing medicaments which act upon the human $GAGA_A$ receptor.

10 Claims, 7 Drawing Sheets

FIGURE 2

```
              10          20          30         41          50         59
                                                  >
GGATCCGTGA ACAGCTTGAA GTATGGCATG TTGCAAAG ATG GTT TCT GCC AAG AAG GTA
                                          MET Val Ser Ala Lys Lys Val 68          77          86         95         104         113
CCC GCG ATC ACT CTG TCC GCC GGG GTC AGT TTC GCC CTC CTG CGC TTC CTG TGC
Pro Ala Ile Thr Leu Ser Ala Gly Val Ser Phe Ala Leu Leu Arg Phe Leu Cys 122        131         140        149         158         167
CTG GCG GTT TGT TTA AAC GAA TCC CCA GGA CAG AAC CAA AAG GAG GAG AAA TTG
Leu Ala Val Cys Leu Asn Glu Ser Pro Gly Gln Asn Gln Lys Glu Glu Lys Leu 176        185         194        203         212         221
TGC ACA GAA AAT TTC ACC CGC ATC CTG GAC AGT TTG CTC GAT GGT TAT GAC AAC
Cys Thr Glu Asn Phe Thr Arg Ile Leu Asp Ser Leu Leu Asp Gly Tyr Asp Asn 230        239         248        257         266         275
AGG CTG CGT CCT GGA TTT GGG GGT CCT GTT ACA GAA GTG AAA ACT GAC ATA TAT
Arg Leu Arg Pro Gly Phe Gly Gly Pro Val Thr Glu Val Lys Thr Asp Ile Tyr 284        293         302        311         320         329
GTC ACC AGC TTT GGA CCT GTT TCT GAT GTT GAA GTG GAA TAC ACA ATG GAT GTG
Val Thr Ser Phe Gly Pro Val Ser Asp Val Glu Val Glu Tyr Thr MET Asp Val 338        347         356        365         374         383
TTC TTC AGG CAG ACA TGG ATT GAC AAA AGA TTA AAA TAT GAC GGC CCC ATT GAA
Phe Phe Arg Gln Thr Trp Ile Asp Lys Arg Leu Lys Tyr Asp Gly Pro Ile Glu 392        401         410        419         428         437
ATT TTG AGA TTG AAC AAT ATG ATG GTA ACG AAA GTG TGG ACC CCT GAT ACT TTC
Ile Leu Arg Leu Asn Asn MET MET Val Thr Lys Val Trp Thr Pro Asp Thr Phe 446        455         464        473         482         491
TTC AGG AAT GGA AAG AAA TCT GTC TCA CAT AAT ATG ACA GCT CCA AAT AAG CTT
Phe Arg Asn Gly Lys Lys Ser Val Ser His Asn MET Thr Ala Pro Asn Lys Leu 500        509         518        527         536         545
TTT AGA ATT ATG AGA AAT GGT ACT ATT TTA TAC ACA ATG AGA CTC ACC ATA AGT
Phe Arg Ile MET Arg Asn Gly Thr Ile Leu Tyr Thr MET Arg Leu Thr Ile Ser 554        563         572        581         590         599
GCG GAG TGT CCC ATG AGA TTG GTG GAT TTT CCC ATG GAT GGT CAT GCA TGC CCT
Ala Glu Cys Pro MET Arg Leu Val Asp Phe Pro MET Asp Gly His Ala Cys Pro 608        617         626        635         644         653
GTG AAA TTC GGG AGT TAT GCC TAT CCA AAG AGT GAG ATG ATC TAT ACC TGG ACA
Val Lys Phe Gly Ser Tyr Ala Tyr Pro Lys Ser Glu MET Ile Tyr Thr Trp Thr
```

FIGURE 2 (CONTINUED)

```
      662           671           680           689           698           707
AAA GGT CCT GAG AAA TCA GTT GAA GTT CCG AAG GAG TCT TCC AGC TTA GTT CAA
Lys Gly Pro Glu Lys Ser Val Glu Val Pro Lys Glu Ser Ser Ser Leu Val Gln 716           725           734           743           752           761
TAT GAT TTG ATT GGG CAA ACC GTA TCA AGT GAA ACC ATC AAA TCA ATT ACG GGT
Tyr Asp Leu Ile Gly Gln Thr Val Ser Ser Glu Thr Ile Lys Ser Ile Thr Gly 770           779           788           797           806           815
GAA TAT ATT GTT ATG ACG GTT TAC TTC CAC CTC AGA CGG AAG ATG GGT TAT TTT
Glu Tyr Ile Val MET Thr Val Tyr Phe His Leu Arg Arg Lys MET Gly Tyr Phe 824           833           842           851           860           869
ATG ATT CAG ACC TAT ATT CCG TGC ATT ATG ACA GTG ATT CTT TCT CAA GTT TCA
MET Ile Gln Thr Tyr Ile Pro Cys Ile MET Thr Val Ile Leu Ser Gln Val Ser 878           887           896           905           914           923
TTT TGG ATA AAT AAA GAA TCA GTT CCC GCT AGG ACC GTA TTT GGA ATA ACA ACT
Phe Trp Ile Asn Lys Glu Ser Val Pro Ala Arg Thr Val Phe Gly Ile Thr Thr 932           941           950           959           968           977
GTC CTC ACC ATG ACC ACA CTA AGC ATC AGT GCA CGA CAT TCT TTG CCC AAA GTG
Val Leu Thr MET Thr Thr Leu Ser Ile Ser Ala Arg His Ser Leu Pro Lys Val 986           995          1004          1013          1022          1031
TCC TAT GCT ACC GCC ATG GAC TGG TTC ATA GCT GTC TGC TTT GCT TTT GTA TTT
Ser Tyr Ala Thr Ala MET Asp Trp Phe Ile Ala Val Cys Phe Ala Phe Val Phe 1040          1049          1058          1067          1076          1085
TCG GCC CTT ATC GAG TTT GCT GCT GTC AAC TAT TTC ACC AAT ATT CAA ATG GAA
Ser Ala Leu Ile Glu Phe Ala Ala Val Asn Tyr Phe Thr Asn Ile Gln MET Glu 1094          1103          1112          1121          1130          1139
AAA GCC AAA AGG AAG ACA TCA AAG CCC CCT CAG GAA GTT CCC GCT GCT CCA GTG
Lys Ala Lys Arg Lys Thr Ser Lys Pro Pro Gln Glu Val Pro Ala Ala Pro Val 1148          1157          1166          1175          1184          1193
CAG AGA GAG AAG CAT CCT GAA GCC CCT CTG CAG AAT ACA AAT GCC AAT TTG AAC
Gln Arg Glu Lys His Pro Glu Ala Pro Leu Gln Asn Thr Asn Ala Asn Leu Asn 1202          1211          1220          1229          1238          1247
ATG AGA AAA AGA ACA AAT GCT TTG GTT CAC TCT GAA TCT GAT GTT GGC AAC AGA
MET Arg Lys Arg Thr Asn Ala Leu Val His Ser Glu Ser Asp Val Gly Asn Arg 1256          1265          1274          1283          1292          1301
ACT GAG GTG GGA AAC CAT TCA AGC AAA TCT TCC ACA GTT GTT CAA GAA TCT TCT
Thr Glu Val Gly Asn His Ser Ser Lys Ser Ser Thr Val Val Gln Glu Ser Ser 1310          1319          1328          1337          1346          1355
AAA GGC ACA CCT CGG TCT TAC TTA GCT TCC AGT CCA AAC CCA TTC AGC CGT GCA
Lys Gly Thr Pro Arg Ser Tyr Leu Ala Ser Ser Pro Asn Pro Phe Ser Arg Ala
```

FIGURE 2 (CONTINUED)

```
       1364         1373         1382         1391         1400         1409
AAT GCA GCT GAA ACC ATA TCT GCA GCA AGA GCA CTT CCA TCT GCT TCT CCT ACT
Asn Ala Ala Glu Thr Ile Ser Ala Ala Arg Ala Leu Pro Ser Ala Ser Pro Thr 1418         1427         1436         1445         1454         1463
TCT ATC CGA ACT GGA TAT ATG CCT CGA AAG GCT TCA GTT GGA TCT GCT TCT ACT
Ser Ile Arg Thr Gly Tyr MET Pro Arg Lys Ala Ser Val Gly Ser Ala Ser Thr 1472         1481         1490         1499         1508         1517
CGT CAC GTG TTT GGA TCA AGA CTG CAG AGG ATA AAG ACC ACA GTT AAT ACC ATA
Arg His Val Phe Gly Ser Arg Leu Gln Arg Ile Lys Thr Thr Val Asn Thr Ile 1526         1535         1544         1553         1562         1571
GGG GCT ACT GGG AAG TTG TCA GCT ACT CCT CCT CCA TCG GCT CCA CCA CCT TCT
Gly Ala Thr Gly Lys Leu Ser Ala Thr Pro Pro Pro Ser Ala Pro Pro Pro Ser 1580         1589         1598         1607         1616         1625
GGA TCT GGC ACA AGT AAA ATA GAC AAA TAT GCC CGT ATT CTC TTT CCA GTC ACA
Gly Ser Gly Thr Ser Lys Ile Asp Lys Tyr Ala Arg Ile Leu Phe Pro Val Thr 1634         1643         1652         1661         1670         1679
TTT GGG GCA TTT AAC ATG GTT TAT TGG GTT GTT TAT TTA TCT AAG GAC ACT ATG
Phe Gly Ala Phe Asn MET Val Tyr Trp Val Val Tyr Leu Ser Lys Asp Thr MET 1688         1697         1707
                                 >
GAG AAA TCA GAA AGT CTA ATG TGA ATTC
Glu Lys Ser Glu Ser Leu MET
```

Figure 3

```
         10          20          30          40          49         58
                                                          >
GAATTCCCCA AGTTTGCGCG GACCCCGTCC CGAGCCCGCC GCGGCC ATG GAC GCG CCC GCC
                                                    MET Asp Ala Pro Ala 67          76          85          94         103        112
CGG CTG CTG GCC CCG CTC CTG CTC CTC TGC GCG CAG CAG CTC CGC GGC ACC AGA
Arg Leu Leu Ala Pro Leu Leu Leu Leu Cys Ala Gln Gln Leu Arg Gly Thr Arg 121         130         139         148         157        166
GCG ATG AAT GAC ATC GGC GAC TAC GTG GGC TCC AAC CTG GAG ATC TCC TGG CTC
Ala MET Asn Asp Ile Gly Asp Tyr Val Gly Ser Asn Leu Glu Ile Ser Trp Leu 175         184         193         202         211        220
CCC AAC CTG GAC GGG CTG ATA GCC GGT TAC GCC CGC AAC TTC CGG CCT GGC ATC
Pro Asn Leu Asp Gly Leu Ile Ala Gly Tyr Ala Arg Asn Phe Arg Pro Gly Ile 229         238         247         256         265        274
GGA GGC CCC CCC GTG AAT GTG GCC CTT GCC CTG GAG GTG GCC AGC ATC GAC CAC
Gly Gly Pro Pro Val Asn Val Ala Leu Ala Leu Glu Val Ala Ser Ile Asp His 283         292         301         310         319        328
ATC TCA GAG GCC AAC ATG GAG TAC ACC ATG ACG GTG TTC CTG CAC CAG AGC TGG
Ile Ser Glu Ala Asn MET Glu Tyr Thr MET Thr Val Phe Leu His Gln Ser Trp 337         346         355         364         373        382
CGG GAC AGC AGG CTC TCC TAC AAC CAC ACC AAC GAG ACC CTG GGC CTG GAC AGC
Arg Asp Ser Arg Leu Ser Tyr Asn His Thr Asn Glu Thr Leu Gly Leu Asp Ser 391         400         409         418         427        436
CGC TTC GTG GAC AAG CTG TGG CTG CCC GAC ACC TTC ATC GTG AAC GCC AAG TCG
Arg Phe Val Asp Lys Leu Trp Leu Pro Asp Thr Phe Ile Val Asn Ala Lys Ser 445         454         463         472         481        490
GCC TGG TTC CAC GAC GTG ACG GTG GAG AAC AAG CTC ATC CGG CTG CAG CCC GAC
Ala Trp Phe His Asp Val Thr Val Glu Asn Lys Leu Ile Arg Leu Gln Pro Asp 499         508         517         526         535        544
GGG GTG ATC CTG TAC AGC ATC CGA ATC ACC TCC ACT GTG GCC TGC GAC ATG GAC
Gly Val Ile Leu Tyr Ser Ile Arg Ile Thr Ser Thr Val Ala Cys Asp MET Asp 553         562         571         580         589        598
CTG GCC AAA TTC CCC ATG GAC GAG CAG GAG TGC ATG CTG GAC CTG GAG AGC TAC
Leu Ala Lys Phe Pro MET Asp Glu Gln Glu Cys MET Leu Asp Leu Glu Ser Tyr 607         616         625         634         643        652
GGT TAC TCA TCG GAG GAC ATC GTC TAC TAC TGG TCG GAG AGC CAG GAG CAC ATC
Gly Tyr Ser Ser Glu Asp Ile Val Tyr Tyr Trp Ser Glu Ser Gln Glu His Ile
```

Figure 3 (continued)

```
  661             670             679             688             697             706
CAC GGG CTG GAC AAG CTG CAG CTG GCG CAG TTC ACC ATC ACC AGC TAC CGC TTC
His Gly Leu Asp Lys Leu Gln Leu Ala Gln Phe Thr Ile Thr Ser Tyr Arg Phe
  715             724             733             742             751             760
ACC ACG GAG CTG ATG AAC TTC AAG TCC GCT GGC CAG TTC CCA CGG CTC AGC CTG
Thr Thr Glu Leu MET Asn Phe Lys Ser Ala Gly Gln Phe Pro Arg Leu Ser Leu
  769             778             787             796             805             814
CAC TTC CAC CTG CGG AGG AAC CGC GGC GTG TAC ATC ATC CAA TCC TAC ATG CCC
His Phe His Leu Arg Arg Asn Arg Gly Val Tyr Ile Ile Gln Ser Tyr MET Pro
  823             832             841             850             859             868
TCC GTC CTG CTG GTC GCC ATG TCC TGG GTC TCC TTC TGG ATC AGC CAG GCG GCG
Ser Val Leu Leu Val Ala MET Ser Trp Val Ser Phe Trp Ile Ser Gln Ala Ala
  877             886             895             904             913             922
GTG CCC GCC AGG GTG TCT CTA GGC ATC ACC ACG GTG CTG ACG ATG ACC ACG CTC
Val Pro Ala Arg Val Ser Leu Gly Ile Thr Thr Val Leu Thr MET Thr Thr Leu
  931             940             949             958             967             976
ATG GTC AGT GCC CGC TCC TCC CTG CCA CGG GCA TCA GCC ATC AAG GCA CTG GAC
MET Val Ser Ala Arg Ser Ser Leu Pro Arg Ala Ser Ala Ile Lys Ala Leu Asp
  985             994            1003            1012            1021            1030
GTC TAC TTC TGG ATC TGC TAT GTC TTC GTG TTT GCC GCC CTG GTG GAG TAC GCC
Val Tyr Phe Trp Ile Cys Tyr Val Phe Val Phe Ala Ala Leu Val Glu Tyr Ala
 1039            1048            1057            1066            1075            1084
TTT GCT CAT TTC AAC GCC GAC TAC AGG AAG AAG CAG AAG GCC AAG GTC AAG GTC
Phe Ala His Phe Asn Ala Asp Tyr Arg Lys Lys Gln Lys Ala Lys Val Lys Val
 1093            1102            1111            1120            1129            1138
TCC AGG CCG AGG GCA GAG ATG GAC GTG AGG AAC GCC ATT GTC CTC TTC TCC CTC
Ser Arg Pro Arg Ala Glu MET Asp Val Arg Asn Ala Ile Val Leu Phe Ser Leu
 1147            1156            1165            1174            1183            1192
TCT GCT GCC GGC GTC ACG CAG GAG CTG GCC ATC TCC CGC CGG CAG CGC CGC GTC
Ser Ala Ala Gly Val Thr Gln Glu Leu Ala Ile Ser Arg Arg Gln Arg Arg Val
 1201            1210            1219            1228            1237            1246
CCG GGG AAC CTG ATG GGC TCC TAC AGG TCG GTG GGG GTG GAG ACA GGG GAG ACG
Pro Gly Asn Leu MET Gly Ser Tyr Arg Ser Val Gly Val Glu Thr Gly Glu Thr
 1255            1264            1273            1282            1291            1300
AAG AAG GAG GGG GCA GCC CGC TCA GGA GGC CAG GGG GGC ATC CGT GCC CGG CTC
Lys Lys Glu Gly Ala Ala Arg Ser Gly Gly Gln Gly Gly Ile Arg Ala Arg Leu
```

Figure 3 (continued)

```
        1309        1318        1327        1336        1345        1354
        AGG CCC ATC GAC GCA GAC ACC ATT GAC ATT TAC GCC CGC GCT GTG TTC CCT GCG
        Arg Pro Ile Asp Ala Asp Thr Ile Asp Ile Tyr Ala Arg Ala Val Phe Pro Ala 1363        1372        1381        1390        1399              1415
                                                                        >
        GCG TTT GCG GCC GTC AAT GTC ATC TAC TGG GCG GCA TAC GCC ATG TGA GCACAGGACT
        Ala Phe Ala Ala Val Asn Val Ile Tyr Trp Ala Ala Tyr Ala MET 1425        1435        1445        1455        1465        1475        1485
     CAGGCCACCC TCGCTTGTCC TGGCGCCCGG CGGCAGCTGC CCAGAAACTT CCTGGGAGAA AGAGCCCTCG 1495        1505        1515        1525        1535        1545        1555
     GGCTGCCTTC CCCTCTGCGT GTTTCGAAGT GGGATGACAG TCGGCCACGG AAAACAAGAG GAAGCCTCGG
```

DELTA SUBUNIT OF HUMAN GABAA RECEPTOR

CROSS-REFERENCE TO RELATED APPLICATIONS

This application is a divisional application of U.S. patent application Ser. No. 08/809,802, filed Jun. 19, 1997, now U.S. Pat. No. 6,455,276 which is PCT application PCT/GB95/02323 filed Sep. 9, 1995 entering the U.S. national phase.

FIELD OF THE INVENTION

This invention concerns the cloning of a novel cDNA sequence encoding a particular subunit of the human $GABA_A$ receptor. In addition, the invention relates to a stable cell line capable of expressing said cDNA and to the use of the cell line in a screening technique for the design and development of subtype-specific medicaments.

BACKGROUND

Gamma-amino butyric acid (GABA) is a major inhibitory neurotransmitter in the central nervous system. It mediates fast synaptic inhibition by opening the chloride channel intrinsic to the $GABA_A$ receptor. This receptor comprises a multimeric protein of molecular size 230–270 kDa with specific binding sites for a variety of drugs including benzodiazepines, barbiturates and β-carbolines, in addition to sites for the agonist ligand GABA (for reviews see Stephenson, *Biochem. J.*, 1988, 249, 21; Olsen and Tobin, *Faseb J.*, 1990, 4, 1469; and Sieghart, *Trends in Pharmacol. Sci.*, 1989, 10, 407).

Molecular biological studies demonstrate that the receptor is composed of several distinct types of subunit, which are divided into four classes (α, β, γ and δ) based on their sequence similarities. To date, six types of α (Schofield et al., *Nature (London)*, 1987, 328, 221; Levitan et al., *Nature (London)*, 1988, 335, 76; Ymer et al., *EMBO J.*, 1989, 8, 1665; Pritchett & Seeberg, *J. Neurochem.*, 1990, 54, 862; Luddens et al., *Nature (London)*, 1990, 346, 648; and Khrestchatisky et al., *Neuron*, 1989, 3, 745), three types of β (Ymer et al., *EMBO J.*, 1989, 8, 1665), three types of γ (Ymer et al., *EMBO J.*, 1990, 9, 3261; Shivers et al., *Neuron*, 1989, 3, 327; and Knoflach et al, *FEBS Lett.*, 1991, 293, 191) and one δ subunit (Shivers et al., *Neuron*, 1989, 3, 327) have been identified.

The differential distribution of many of the subunits has been characterised by in situ hybridisation (Sequier et al., *Proc. Natl. Acad. Sci. USA*, 1988, 85, 7815; Malherbe et al., *J. Neurosci.*, 1990, 10, 2330; Shivers et al., *Neuron*, 1989, 3, 327; and Wisden et al, *J. Neurosci.*, 1992, 12, 1040) and this has permitted it to be speculated which subunits, by their co-localisation, could theoretically exist in the same receptor complex.

Various combinations of subunits have been co-transfected into cells to identify synthetic combinations of subunits whose pharmacology parallels that of bona fide $GABA_A$ receptors in vivo (Pritchett et al., *Science*, 1989, 245, 1389; Malherbe et al., *J. Neurosci.*, 1990, 10, 2330; Pritchett and Seeberg, *J. Neurochem.*, 1990, 54, 1802; and Luddens et al., *Nature (London)*, 1990, 346, 648). This approach has revealed that, in addition to an α and β subunit, either $\gamma_1$ or $\gamma_2$ (Pritchett et al., *Nature (London)*, 1989, 338, 582; Ymer et al., *EMBO J.*, 1990, 9, 3261; and Malherbe et al., *J. Neurosci.*, 1990, 10, 2330) or $\gamma_3$ (Herb et al., *Proc. Natl. Acad. Sci. USA*, 1992, 89, 1433; Knoflach et al., *FEBS Lett.*, 1991, 293, 191; and Wilson-Shaw et al., *FEBS Lett.*, 1991, 284, 211) is also generally required to confer benzodiazepine sensitivity, and that the benzodiazepine pharmacology of the expressed receptor is largely dependent on the identity of the α and γ subunits present. Receptors containing a δ subunit (i.e. αβδ) do not appear to bind benzodiazepines (Shivers et al., *Neuron*, 1989, 3, 327). Combinations of subunits have been identified which exhibit the pharmacological profile of a $BZ_1$ type receptor ($\alpha_1\beta_2\gamma_2$) and a $BZ_2$ type receptor ($\alpha_2\beta_1\gamma_2$ or $\alpha_3\beta_1\gamma_2$, Pritchett et al., *Nature (London)*, 1989, 338, 582), as well as two $GABA_A$ receptors with a novel pharmacology, $\alpha_5\beta_2\gamma_2$ (Pritchett and Seeberg, *J. Neurochem.*, 1990, 54, 1802) and $\alpha_6\beta_2\gamma_2$ (Luddens et al., *Nature (London)*, 1990, 346, 648). Although the pharmacology of these expressed receptors appears similar to that of those identified in brain tissue by radioligand binding, it has nonetheless not been shown that these receptor subunit combinations exist in vivo.

SUMMARY OF THE INVENTION

A combination of subunits comprising either the human $\alpha_4$ $GABA_A$ receptor subunit and/or the δ $GABA_A$ receptor subunit has not hitherto been possible due to the non-availability of the human $\alpha_4$ cDNA or human δ cDNA. This has consequently limited the use of cell lines in screening for subtype-specific medicaments, it being impossible to study the pharmacological profile of subunit combinations comprising the $\alpha_4$ subunit and/or the δ subunit.

We have now ascertained the cDNA sequence of the $\alpha_4$ subunit and the δ subunit of the human $GABA_A$ receptor. These nucleotide sequences (SEQ ID NO:7 and SEQ ID NO:11), together with their deduced amino acid sequences (SEQ ID NO:8 and SEQ ID NO:12) corresponding thereto, are depicted in FIGS. 2 and 3 of the accompanying drawings.

The present invention accordingly provides, in a first aspect, a DNA molecule encoding the $\alpha_4$ subunit of the human $GABA_A$ receptor comprising all or a portion of the sequence (SEQ ID NO:7) depicted in FIG. 2, or a modified human sequence.

The present invention also provides, in another aspect, a DNA molecule encoding the δ subunit of the human $GABA_A$ receptor comprising all or a portion of the sequence (SEQ ID NO:11) depicted in FIG. 3, or a modified human sequence.

The sequencing of the novel cDNA molecules in accordance with the invention can conveniently be carried out by the standard procedure described in accompanying Example 1; or may be accomplished by alternative molecular cloning techniques which are well known in the art, such as those described by Maniatis et al. in *Molecular Cloning, A Laboratory Manual*, Cold Spring Harbor Press, New York, 2nd edition, 1989.

In another aspect, the invention provides a recombinant expression vector comprising the nucleotide sequence of the human $GABA_A$ receptor $\alpha_4$ subunit together with additional sequences capable of directing the synthesis of the said human $GABA_A$ receptor $\alpha_4$ subunit in cultures of stably co-transfected eukaryotic cells.

The present invention also provides a recombinant expression vector comprising the nucleotide sequence of the human $GABA_A$ receptor δ subunit together with additional sequences capable of directing the synthesis of the said human $GABA_A$ receptor δ subunit in cultures of stably co-transfected eukaryotic cells.

BRIEF DESCRIPTION OF THE DRAWINGS

FIG. 2 depicts the nucleotide sequence (SEQ ID NO:7) of the $\alpha_4$ receptor subunit cDNA and the amino acid sequence (SEQ ID NO:8) of the encoded polypeptide.

FIG. 3 depicts the nucleotide sequence (SEQ ID NO:11) of the $\delta$ receptor subunit cDNA and the amino acid sequence (SEQ ID NO:12) of the encoded polypeptide.

DETAILED DESCRIPTION OF THE INVENTION

Figure 1:
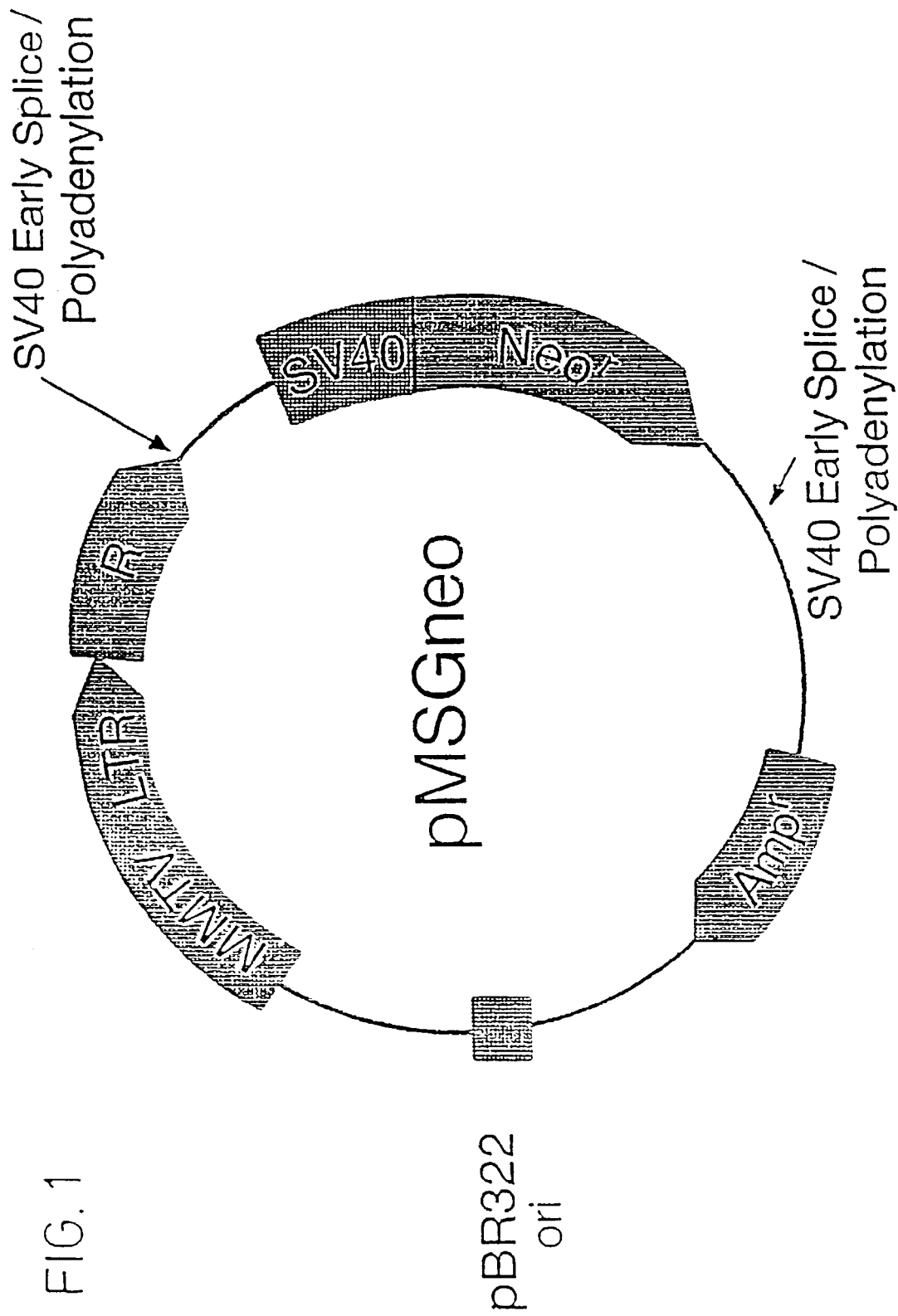
FIG. 1 depicts an expression vector in which R represents the nucleotide sequence of the $\alpha_4$ or $\delta$ subunit of the GABA$_A$ receptor, and the remainder of the expression vector is derived from the precursor vector pMSGneo.

The present invention provides nucleotide sequences encoding the $\alpha_4$ and $\delta$ subunits of the human GABA$_A$ receptor, preparations of $\alpha_4$ and $\delta$ receptor subunit proteins, preparations of receptors including $\alpha_4$ or $\delta$ polypeptides, expression vectors including the nucleotide sequences, stably co-transfected eukaryotic cells and methods of their preparation and methods of screening for and designing medicaments which act upon the GABA$_A$ receptor.

The term "expression vectors" as used herein refers to DNA sequences that are required for the transcription of cloned copies of recombinant DNA sequences or genes and the translation of their mRNAs in an appropriate host. Such vectors can be used to express eukaryotic genes in a variety of hosts such as bacteria, blue-green algae, yeast cells, insect cells, plant cells and animal cells. Specifically designed vectors allow the shuttling of DNA between bacteria-yeast, bacteria-plant or bacteria-animal cells. An appropriately constructed expression vector should contain: an origin of replication for autonomous replication in host cells, selective markers, a limited number of useful restriction enzyme sites, a high copy number, and strong promoters. A promoter is defined as a DNA sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses.

The term "cloning vector" as used herein refers to a DNA molecule, usually a small plasmid or bacteriophage DNA capable of self-replication in a host organism, and used to introduce a fragment of foreign DNA into a host cell. The foreign DNA combined with the vector DNA constitutes a recombinant DNA molecule which is derived from recombinant technology. Cloning vectors may include plasmids, bacteriophages, viruses and cosmids.

The recombinant expression vector in accordance with the invention may be prepared by inserting the nucleotide sequence of the GABA$_A$ $\alpha_4$ subunit or the GABA$_A$ $\delta$ subunit into a suitable precursor expression vector (hereinafter referred to as the "precursor vector") using conventional recombinant DNA methodology known from the art. The precursor vector may be obtained commercially, or constructed by standard techniques from known expression vectors. The precursor vector suitably contains a selection marker, typically an antibiotic resistance gene, such as the neomycin or ampicillin resistance gene. The precursor vector preferably contains a neomycin resistance gene, adjacent the SV40 early splicing and polyadenylation region; an ampicillin resistance gene; and an origin of replication, e.g. pBR322 ori. The vector also preferably contains an inducible promoter, such as MMTV-LTR (inducible with dexamethasone) or metallothionin (inducible with zinc), so that transcription can be controlled in the cell line of this invention. This reduces or avoids any problem of toxicity in the cells because of the chloride channel intrinsic to the GABA$_A$ receptor.

One suitable precursor vector is pMAMneo, available from Clontech Laboratories Inc. (Lee et al., *Nature*, 1981, 294, 228; and Sardet et al., *Cell*, 1989, 56, 271). Alternatively the precursor vector pMSGneo can be constructed from the vectors pMSG and pSV2neo.

The recombinant expression vector of the present invention is then produced by cloning the GABA$_A$ receptor $\alpha_4$ subunit cDNA or the GABA$_A$ receptor $\delta$ subunit cDNA into the above precursor vector. The receptor subunit cDNA is subcloned from the vector in which it is harboured, and ligated into a restriction enzyme site, e.g. the Hind III site, in the polylinker of the precursor vector, for example pMAMneo or pMSGneo, by standard cloning methodology known from the art, and in particular by techniques analogous to those described herein. Before this subcloning, it is often advantageous, in order to improve expression, to modify the end of the $\alpha_4$ or $\delta$ subunit cDNA with additional 5' untranslated sequences, for example by modifying the 5' end of the $\alpha_4$ or $\delta$ subunit DNA by addition of 5' untranslated region sequences from the $\alpha_1$ subunit DNA.

One suitable expression vector of the present invention is illustrated in FIG. 1 of the accompanying drawings, in which R represents the nucleotide sequence of the $\alpha_4$ or $\delta$ subunit of the GABA$_A$ receptor, and the remainder of the expression vector depicted therein is derived from the precursor vector pMSGneo.

According to a further aspect of the present invention, there is provided a stably co-transfected eukaryotic cell line capable of expressing a GABA$_A$ receptor, which receptor comprises the alpha-4 receptor subunit, at least one beta receptor subunit and the delta receptor subunit.

In another aspect of the present invention, there is provided a stably co-transfected eukaryotic cell line capable of expressing a GABA$_A$ receptor, which receptor comprises the alpha-4 receptor subunit, at least one beta receptor subunit and at least one gamma receptor subunit.

In a further aspect of the present invention, there is provided a stably co-transfected eukaryotic cell line capable of expressing a GABA$_A$ receptor, which receptor comprises at least one alpha receptor subunit, at least one beta receptor subunit and the delta receptor subunit.

This is achieved by co-transfecting cells with three expression vectors, each harbouring cDNAs encoding for an $\alpha_4$, $\beta$ or $\delta$ GABA$_A$ receptor subunit, or for an $\alpha_4$, $\beta$ or $\gamma$ GABA$_A$ receptor subunit, or for an $\alpha$, $\beta$ or $\delta$ GABA$_A$ receptor subunit. In a further aspect, therefore, the present invention provides a process for the preparation of a eukaryotic cell line capable of expressing a GABA$_A$ receptor, which comprises stably co-transfecting a eukaryotic host cell with at least three expression vectors, one such vector harbouring the cDNA sequence encoding the $\alpha_4$ GABA$_A$ receptor subunit another such vector harbouring the cDNA sequence encoding a beta GABA$_A$ receptor subunit, and a third such vector harbouring the cDNA sequence encoding the delta GABA$_A$ receptor subunit. The stable cell-line which is established expresses an $\alpha_4\beta\delta$ GABA$_A$ receptor.

The present invention also provides a process for the preparation of a eukaryotic cell line capable of expressing a GABA$_A$ receptor, which comprises stably co-transfecting a eukaryotic host cell with at least three expression vectors, one such vector harbouring the cDNA sequence encoding the $\alpha_4$ GABA$_A$ receptor subunit another such vector harbouring the cDNA sequence encoding a beta $GABA_A$ receptor subunit, and a third such vector harbouring the cDNA sequence encoding a gamma $GABA_A$ receptor subunit. The stable cell-line which is established expresses an $\alpha_4\beta\gamma$ $GABA_A$ receptor.

Similarly, the present invention provides a process for the preparation of a eukaryotic cell line capable of expressing a $GABA_A$ receptor, which comprises co-transfecting a eukaryotic host cell with at least three expression vectors, one such vector harbouring the cDNA sequence encoding an alpha $GABA_A$ receptor subunit, another such vector harbouring the cDNA sequence encoding a beta $GABA_A$ receptor subunit, and a third such vector harbouring the cDNA sequence encoding the $\delta$ $GABA_A$ receptor subunit. The stable cell line which is established expresses an $\alpha\beta\delta$ $GABA_A$ receptor.

Each receptor thereby expressed, comprising a unique combination of $\alpha_4$, $\beta$ and $\delta$ subunits, or $\alpha_4$, $\beta$ and $\gamma$ subunits, or $\alpha$, $\beta$ and $\delta$ subunits, will be referred to hereinafter as a $GABA_A$ receptor "subunit combination". Pharmacological and electrophysiological data confirm that the recombinant $\alpha_4\beta\gamma$ receptor expressed by the cells of the present invention has the properties expected of a native $GABA_A$ receptor.

Expression of the $GABA_A$ receptor may be accomplished by a variety of different promoter-expression systems in a variety of different host cells. The eukaryotic host cells suitably include yeast, insect and mammalian cells. Preferably the eukaryotic cells which can provide the host for the expression of the receptor are mammalian cells. Suitable host cells include rodent fibroblast lines, for example mouse Ltk$^-$, Chinese hamster ovary (CHO) and baby hamster kidney (BHK); HeLa; and HEK293 cells. It is necessary to incorporate the ($\alpha_4$ subunit, at least one $\beta$ and the $\delta$ subunit into the cell line in order to produce the required receptor, or alternatively the $\alpha_4$ subunit and at least one $\beta$ and one $\gamma$ subunit or alternatively at least one $\alpha$, one $\beta$ and the $\delta$ subunit. Within this limitation, the choice of receptor subunit combination is made according to the type of activity or selectivity which is being screened for.

In order to employ this invention most effectively for screening purposes, it is preferable to build up a library of cell lines, each with a different combination of subunits. Typically a library of 5 or 6 cell line types is convenient for this purpose. Preferred subunit combinations include: $\alpha_4\beta_3\gamma_2$, $\alpha_4\beta_3\delta$ and $\alpha_6\beta_3\delta$. Another preferred subunit combination is $\alpha_4\beta_2\gamma_2$.

As stated above, for each cell line of the present invention, three such vectors will be necessary, one containing the $\alpha_4$ subunit, one containing a $\beta$ subunit, and the third containing the $\delta$ subunit, or alternatively, one containing the $\alpha_4$ subunit, one containing a $\beta$ subunit, and the third containing a $\gamma$ subunit, or alternatively, one containing an $\alpha$ subunit, one containing $\beta$ subunit and one containing the $\delta$ subunit.

Cells are then co-transfected with the desired combination of three expression vectors. There are several commonly used techniques for transfection of eukaryotic cells in vitro. Calcium phosphate precipitation of DNA is most commonly used (Bachetti et al., *Proc. Natl. Acad. Sci. USA,* 1977, 74, 1590–1594; Maitland et al., *Cell,* 1977, 14, 133–141), and represents a favoured technique in the context of the present invention.

A small percentage of the host cells takes up the recombinant DNA. In a small percentage of those, the DNA will integrate into the host cell chromosome. Because the neomycin resistance gene will have been incorporated into these host cells, they can be selected by isolating the individual clones which will grow in the presence of neomycin. Each such clone is then tested to identify those which will produce the receptor. This is achieved by inducing the production, for example with dexamethasone, and then detecting the presence of receptor by means of radioligand binding.

In a further aspect, the present invention provides protein preparations of $GABA_A$ receptor subunit combinations, especially human $GABA_A$ receptor subunit combinations, derived from cultures of stably transfected eukaryotic cells. The invention also provides preparations of membranes containing subunit combinations of the $GABA_A$ receptor, especially human $GABA_A$ receptor subunit combinations, derived from cultures of stably transfected eukaryotic cells.

The cell line, and the membrane preparations therefrom, according to the present invention have utility in screening and design of drugs which act upon the $GABA_A$ receptor, for example benzodiazepines, barbiturates, $\beta$-carbolines and neurosteroids. The present invention accordingly provides the use of the cell line described above, and membrane preparations derived therefrom, in screening for and designing medicaments which act upon the $GABA_A$ receptor. Of particular interest in this context are molecules capable of interacting selectively with $GABA_A$ receptors made up of varying subunit combinations. As will be readily apparent, the cell line in accordance with the present invention, and the membrane preparations derived therefrom, provide ideal systems for the study of structure, pharmacology and function of the various $GABA_A$ receptor subtypes.

The following non-limiting Examples illustrate the present invention.

EXAMPLE 1

Isolation and Sequencing of cDNAs Encoding the Human $GABA_A$ Receptor $\alpha_4$ Subunit a) cDNA Libraries cDNAs were cloned from human foetal brain and adult hippocampus cDNA libraries. All cDNA libraries were constructed in the lambdaZAP vector, and were purchased from Stratagene (San Diego, Calif.). For screening, the cDNA libraries were plated according to the manufacturer's instructions, at 40,000 pfu per 137 mm plate. Filter lifts were taken using Hybond N filters (Amersham) according to the manufacturer's instructions.

b) Isolation of cDNA Encoding Human $\alpha_4$ Subunit

A human $\alpha_4$ probe was first generated by polymerase chain reaction (PCR) using oligonucleotide primers (synthesised on an Applied Biosystems 380B synthesizer) derived from the bovine $\alpha_4$ sequence (Ymer et al, *FEBS Lett.,* 1989, 258, 119): 5'TTTCAGGAATTCCAGTGCT-GAGAGAAAAGCATCCTGAAAC3' (bp 1121–1160, containing an EcoRI restriction enzyme site) SEQ. ID. NO.:1, and 5'ATCCAGAAGCTTGTGGAGCAGAGGGAG-TAGTAGTGGC3' (antisense, bp 1540–1577, incorporating a HindIII restriction enzyme site) SEQ. ID. NO.:2. PCR was performed as described, for example, by Whiting et al in *Proc. Natl. Acad. Sci., USA,* 1990, 87, 9966, using a human foetal brain cDNA library as a template. The PCR product was digested with EcoRI and HindIII and subcloned into similarly digested pBluescript SK- and its identity confirmed by DNA sequencing using standard techniques and the Sequenase II enzyme (United States Biochemicals).

A human foetal brain cDNA library was screened using $^{32}$P labelled human $\alpha_4$ probe DNA as described above. A single cDNA clone, approximately 2500 bp, was obtained. DNA sequencing indicated that this cDNA clone contained 3' untranslated sequences and 3' coding region up to bp 1162 of the bovine cDNA sequence. The missing 5' sequence was obtained by anchored PCR using human brain 5'-RACE-Ready cDNA (CLONTECH, Palo Alto, Calif.), according to the manufacturer's instructions. The antisense oligonucleotides used for nested PCR were 5'ATTGGCATTTGTATTCTGCAGAGG3' SEQ. ID. NO.:3, and 5'GGAAGATTTGCTTGAATGGTTTGG3' SEQ. ID. NO.:4. A 1200 bp PCR product was obtained. DNA sequencing confirmed that this cDNA contained the missing 5' sequence of the $\alpha_4$ cDNA, extending to 130 bp 5' of the initiating ATG codon.

A full length $\alpha_4$ cDNA was generated by PCR using oligonucleotide primers generated from sequences of the 5' and 3' untranslated region: 5' sense primer 5'CCTGGATCCGTGAACAGGCTTGAAGTATG3' (incorporating a BamHI restriction enzyme site) SEQ. ID. NO.:5; 3' antisense primer 5'ACGAATTCACATTAGACTTTCTGATTTCTC3' (incorporating an EcoRI restriction enzyme site) SEQ. ID. NO.:6. PCR was performed using human brain thalamus cDNA. A 1500 bp product was generated which was subcloned into the cloning/eukaryotic expression vector pcDNA/Amp (Invitrogen). The cDNA was sequenced completely on both strands using an Applied Biosystems 373A DNA sequencer and dye terminator chemistry according to the manufacturer's instructions.

The complete nucleotide sequence of the cDNA encoding the human $\alpha_4$ subunit, together with the deduced amino acid sequence corresponding thereto is shown in FIG. 2 of the accompanying drawings SEQ. ID. NOS.:7 and 8.

EXAMPLE 2

Isolation and Sequencing of cDNAs Encoding the Human GABA$_A$ Receptor δ Subunit a) cDNA Libraries As described in Example 1(a).

b) Isolation of cDNA Encoding Human δ Subunit

A rat δ subunit probe was first generated by PCR using oligonucleotide primers derived from the rat δ subunit sequence (Shivers et al, *Neuron*, 1989, 3, 327): 5'AGCCCGAATTCCATGGACGTTCTGGGCTGGCTG3' (bp 18–51, incorporating an EcoRI restriction enzyme site) SEQ. ID. NO.:9 and 5'GGTTTCCAAGCTTACTTTGGAGAGGTAGC3' (bp 1357–1390, incorporating a HindIII restriction enzyme site) SEQ. ID. NO.:10. PCR was performed as described, for example, by Whiting et al, *Proc. Natl. Acad. Sci., USA*, 1990, 87, 9966, using rat brain cDNA as template. A 1400 bp product was obtained, subcloned into pBluescript SK- and its identity confirmed by DNA sequencing. A human hippocampus cDNA library was screened using $^{32}$P labelled rat δ subunit probe DNA as described above. A single clone was obtained containing an 1800 bp insert. DNA sequencing indicated that this cDNA contained the complete coding region of the human δ subunit. The cDNA was sequenced completely on both strands using an Applied Biosystems 373A DNA sequencer and dye terminator chemistry according to the manufacturer's instructions.

The complete nucleotide sequence of the cDNA encoding the human δ subunit, together with the deduced amino acid sequence corresponding thereto is shown in FIG. 3 of the accompanying drawings SEQ. ID. NOS.:11 and 12.

EXAMPLE 3

Expression of Human $\alpha_4$ cDNA in *Xenopus* Oocytes

The human α4 cDNA (Example 1, FIG. 2) was subcloned into the eukaryotic expresion vector, pcDNA I Amp (Invitrogen, San Diego Calif.). Expression of this cDNA was investigated using the *Xenopus* oocyte system. Methods for preparation of *Xenopus* oocytes, nuclear injection of cDNAs, and eletrophysiological recordings from oocytes expressing recombinant GABA$_A$ receptors, are well documented (see, for instance, Hadingham et al., *Mol. Pharmacol.*, 1993, 44, 1211–1218).

When co-expressed with $\beta_2$ and $\gamma_2$ cDNAs (Hadingham et al., *Mol. Pharmacol.*, 1993, 44, 1211–1218) minimal expressed of GABA$_A$ gated chloride currents were observed (10–50 nA whole cell currents as measured under voltage clamped conditions). To increase the efficiency of expression the $\alpha_4$ cDNA was re-engineered so as to replace the 5' untranslated sequence and signal peptide with the corresponding $\alpha_1$ sequence. PCR was performed using the $\alpha_1$ cDNA (Schofield et al., *Nature (London)*, 1987, 328, 221) as template. Primers were (i) 5'TAATGAGTTTAAACCATAGCTTCTTCCAGT3' (bp 12–35 of $\alpha_1$ incorporating a BamHI site) SEQ. ID. NO.:11, and (ii) 5'CATGATGGATCCGCCCGCTCAGAC3' (bp 269–305 incorporating a PmeI site) SEQ. ID. NO.:12. The BamHI-PmeI cut PCR fragment was subcloned into similarly cut $\alpha_4$ pCDNA I Amp. When this $\alpha_4$ construct was co-expressed in *Xenopus* oocytes with $\beta_2$ and $\gamma_2$ cDNAs robust GABA$_A$ gated currents of up to 1000 nA whole cell current were obtained.

The invention claimed is:

1. An isolated DNA molecule comprising the nucleotide sequence encoding a δ subunit of a human $GABA_A$ receptor provided by SEQ ID NO 12.

2. An isolated stably co-transfected eukaryotic cell line expressing a human $GABA_A$ receptor comprising cDNA encoding the δ receptor subunit of SEQ ID NO: 12, cDNA encoding at least one α receptor subunit, and cDNA encoding at least one β receptor subunit.

3. The cell line of claim 2, wherein said cell line is a rodent fibroblast cell line.

4. A process for the preparation of an isolated eucaryotic cell line expressing a human $GABA_A$ receptor comprising stably co-transfecting a eukaryotic host cell with at least one recombinant expression vector comprising a human cDNA sequence encoding the δ receptor subunit of SEQ ID NO: 12, at least one recombinant expression vector comprising a human cDNA sequence encoding an α receptor subunit, and at least one recombinant expression vector comprising a human cDNA sequence encoding a β receptor subunit.

5. The process of claim 4, wherein said cell line is a rodent fibroblast cell line.

6. A recombinant expression vector comprising a the nucleotide sequence encoding a δ subunit of a human $GABA_A$ receptor provided by SEQ ID NO: 12 together with additional sequences capable of directing the synthesis of said δ receptor subunit in a culture of isolated stably co-transfected eukaryotic cells.

7. An isolated protein preparation of human $GABA_A$ receptor derived from a culture of eukaryotic cells stably transfected with cDNA encoding a human $GABA_A$ receptor, wherein said $GABA_A$ receptor has a subunit combination that includes the human δ receptor subunit of SEQ ID NO: 12, provided that said culture of eukaryotic cells does not endogenously express said human $GABA_A$ receptor.

8. The protein preparation of claim 7, wherein said subunit combination is selected from the group consisting of $\alpha_4\beta_3\delta$ and $\alpha_6\beta_3\delta$.

9. An isolated membrane preparation wherein the membrane preparation comprises a human $GABA_A$ receptor comprising the human δ receptor subunit of SEQ ID NO:12, derived from an isolated culture of eukaryotic cells stably transfected with cDNA encoding a human $GABA_A$ receptors wherein said $GABA_A$ receptor has a subunit combination that includes the human δ receptor subunit of SEQ ID NO: 12, provided that said culture of eukaryotic cells does not endogenously express said human $GABA_A$ receptor.

10. The membrane preparation of claim 9, wherein said subunit combination is selected from the group consisting of $\alpha_4\beta_3\delta$ and $\alpha_6\beta_3\delta$.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

TTTCAGGAAT TCCAGTGCTG AGAGAAAAGC ATCCTGAAAC                                40

(2) INFORMATION FOR SEQ ID NO: 2:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 2:

ATCCAGAAGC TTGTGGAGCA GAGGGAGTAG TAGTGGC                                   37

(2) INFORMATION FOR SEQ ID NO: 3:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 3:

ATTGGCATTT GTATTCTGCA GAGG                                                 24

(2) INFORMATION FOR SEQ ID NO: 4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 4:

GGAAGATTTG CTTGAATGGT TTGG                                                 24

(2) INFORMATION FOR SEQ ID NO: 5:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 5:

CCTGGATCCG TGAACAGGCT TGAAGTATG                                            29

(2) INFORMATION FOR SEQ ID NO: 6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 6:

ACGAATTCAC ATTAGACTTT CTGATTTCTC                                           30

-continued (2) INFORMATION FOR SEQ ID NO: 7:

(i) SEQUENCE CHARACTERISTICS:
        (A) LENGTH: 1707 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 39...1700
        (D) OTHER INFORMATION:

(xi) SEQUENCE DESCRIPTION: SEQ ID NO: 7:

```
GGATCCGTGA ACAGCTTGAA GTATGGCATG TTGCAAAG ATG GTT TCT GCC AAG AA         56
                                         Met Val Ser Ala Lys Lys
                                           1               5

GTA CCC GCG ATC ACT CTG TCC GCC GGG GTC AGT TTC GCC CTC CTG CGC        104
Val Pro Ala Ile Thr Leu Ser Ala Gly Val Ser Phe Ala Leu Leu Arg
                 10                  15                  20

TTC CTG TGC CTG GCG GTT TGT TTA AAC GAA TCC CCA GGA CAG AAC CAA        152
Phe Leu Cys Leu Ala Val Cys Leu Asn Glu Ser Pro Gly Gln Asn Gln
         25                  30                  35

AAG GAG GAG AAA TTG TGC ACA GAA AAT TTC ACC CGC ATC CTG GAC AGT        200
Lys Glu Glu Lys Leu Cys Thr Glu Asn Phe Thr Arg Ile Leu Asp Ser
 40                  45                  50

TTG CTC GAT GGT TAT GAC AAC AGG CTG CGT CCT GGA TTT GGG GGT CCT        248
Leu Leu Asp Gly Tyr Asp Asn Arg Leu Arg Pro Gly Phe Gly Gly Pro
 55                  60                  65                  70

GTT ACA GAA GTG AAA ACT GAC ATA TAT GTC ACC AGC TTT GGA CCT GTT        296
Val Thr Glu Val Lys Thr Asp Ile Tyr Val Thr Ser Phe Gly Pro Val
                 75                  80                  85

TCT GAT GTT GAA GTG GAA TAC ACA ATG GAT GTG TTC TTC AGG CAG ACA        344
Ser Asp Val Glu Val Glu Tyr Thr Met Asp Val Phe Phe Arg Gln Thr
                 90                  95                 100

TGG ATT GAC AAA AGA TTA AAA TAT GAC GGC CCC ATT GAA ATT TTG AGA        392
Trp Ile Asp Lys Arg Leu Lys Tyr Asp Gly Pro Ile Glu Ile Leu Arg
                105                 110                 115

TTG AAC AAT ATG ATG GTA ACG AAA GTG TGG ACC CCT GAT ACT TTC TTC        440
Leu Asn Asn Met Met Val Thr Lys Val Trp Thr Pro Asp Thr Phe Phe
120                 125                 130

AGG AAT GGA AAG AAA TCT GTC TCA CAT AAT ATG ACA GCT CCA AAT AAG        488
Arg Asn Gly Lys Lys Ser Val Ser His Asn Met Thr Ala Pro Asn Lys
135                 140                 145                 150

CTT TTT AGA ATT ATG AGA AAT GGT ACT ATT TTA TAC ACA ATG AGA CTC        536
Leu Phe Arg Ile Met Arg Asn Gly Thr Ile Leu Tyr Thr Met Arg Leu
                155                 160                 165

ACC ATA AGT GCG GAG TGT CCC ATG AGA TTG GTG GAT TTT CCC ATG GAT        584
Thr Ile Ser Ala Glu Cys Pro Met Arg Leu Val Asp Phe Pro Met Asp
                170                 175                 180

GGT CAT GCA TGC CCT GTG AAA TTC GGG AGT TAT GCC TAT CCA AAG AGT        632
Gly His Ala Cys Pro Val Lys Phe Gly Ser Tyr Ala Tyr Pro Lys Ser
                185                 190                 195

GAG ATG ATC TAT ACC TGG ACA AAA GGT CCT GAG AAA TCA GTT GAA GTT        680
Glu Met Ile Tyr Thr Trp Thr Lys Gly Pro Glu Lys Ser Val Glu Val
200                 205                 210

CCG AAG GAG TCT TCC AGC TTA GTT CAA TAT GAT TTG ATT GGG CAA ACC        728
Pro Lys Glu Ser Ser Ser Leu Val Gln Tyr Asp Leu Ile Gly Gln Thr
215                 220                 225                 230

GTA TCA AGT GAA ACC ATC AAA TCA ATT ACG GGT GAA TAT ATT GTT ATG        776
```

-continued

| | | |
|---|---|---|
| Val Ser Ser Glu Thr Ile Lys Ser Ile Thr Gly Glu Tyr Ile Val Met<br>235 240 245 | | |
| ACG GTT TAC TTC CAC CTC AGA CGG AAG ATG GGT TAT TTT ATG ATT CAG<br>Thr Val Tyr Phe His Leu Arg Arg Lys Met Gly Tyr Phe Met Ile Gln<br>250 255 260 | 824 | |
| ACC TAT ATT CCG TGC ATT ATG ACA GTG ATT CTT TCT CAA GTT TCA TTT<br>Thr Tyr Ile Pro Cys Ile Met Thr Val Ile Leu Ser Gln Val Ser Phe<br>265 270 275 | 872 | |
| TGG ATA AAT AAA GAA TCA GTT CCC GCT AGG ACC GTA TTT GGA ATA ACA<br>Trp Ile Asn Lys Glu Ser Val Pro Ala Arg Thr Val Phe Gly Ile Thr<br>280 285 290 | 920 | |
| ACT GTC CTC ACC ATG ACC ACA CTA AGC ATC AGT GCA CGA CAT TCT TTG<br>Thr Val Leu Thr Met Thr Thr Leu Ser Ile Ser Ala Arg His Ser Leu<br>295 300 305 310 | 968 | |
| CCC AAA GTG TCC TAT GCT ACC GCC ATG GAC TGG TTC ATA GCT GTC TGC<br>Pro Lys Val Ser Tyr Ala Thr Ala Met Asp Trp Phe Ile Ala Val Cys<br>315 320 325 | 1016 | |
| TTT GCT TTT GTA TTT TCG GCC CTT ATC GAG TTT GCT GCT GTC AAC TAT<br>Phe Ala Phe Val Phe Ser Ala Leu Ile Glu Phe Ala Ala Val Asn Tyr<br>330 335 340 | 1064 | |
| TTC ACC AAT ATT CAA ATG GAA AAA GCC AAA AGG AAG ACA TCA AAG CCC<br>Phe Thr Asn Ile Gln Met Glu Lys Ala Lys Arg Lys Thr Ser Lys Pro<br>345 350 355 | 1112 | |
| CCT CAG GAA GTT CCC GCT GCT CCA GTG CAG AGA GAG AAG CAT CCT GAA<br>Pro Gln Glu Val Pro Ala Ala Pro Val Gln Arg Glu Lys His Pro Glu<br>360 365 370 | 1160 | |
| GCC CCT CTG CAG AAT ACA AAT GCC AAT TTG AAC ATG AGA AAA AGA ACA<br>Ala Pro Leu Gln Asn Thr Asn Ala Asn Leu Asn Met Arg Lys Arg Thr<br>375 380 385 390 | 1208 | |
| AAT GCT TTG GTT CAC TCT GAA TCT GAT GTT GGC AAC AGA ACT GAG GTG<br>Asn Ala Leu Val His Ser Glu Ser Asp Val Gly Asn Arg Thr Glu Val<br>395 400 405 | 1256 | |
| GGA AAC CAT TCA AGC AAA TCT TCC ACA GTT GTT CAA GAA TCT TCT AAA<br>Gly Asn His Ser Ser Lys Ser Ser Thr Val Val Gln Glu Ser Ser Lys<br>410 415 420 | 1304 | |
| GGC ACA CCT CGG TCT TAC TTA GCT TCC AGT CCA AAC CCA TTC AGC CGT<br>Gly Thr Pro Arg Ser Tyr Leu Ala Ser Ser Pro Asn Pro Phe Ser Arg<br>425 430 435 | 1352 | |
| GCA AAT GCA GCT GAA ACC ATA TCT GCA GCA AGA GCA CTT CCA TCT GCT<br>Ala Asn Ala Ala Glu Thr Ile Ser Ala Ala Arg Ala Leu Pro Ser Ala<br>440 445 450 | 1400 | |
| TCT CCT ACT TCT ATC CGA ACT GGA TAT ATG CCT CGA AAG GCT TCA GTT<br>Ser Pro Thr Ser Ile Arg Thr Gly Tyr Met Pro Arg Lys Ala Ser Val<br>455 460 465 470 | 1448 | |
| GGA TCT GCT TCT ACT CGT CAC GTG TTT GGA TCA AGA CTG CAG AGG ATA<br>Gly Ser Ala Ser Thr Arg His Val Phe Gly Ser Arg Leu Gln Arg Ile<br>475 480 485 | 1496 | |
| AAG ACC ACA GTT AAT ACC ATA GGG GCT ACT GGG AAG TTG TCA GCT ACT<br>Lys Thr Thr Val Asn Thr Ile Gly Ala Thr Gly Lys Leu Ser Ala Thr<br>490 495 500 | 1544 | |
| CCT CCT CCA TCG GCT CCA CCA CCT TCT GGA TCT GGC ACA AGT AAA ATA<br>Pro Pro Pro Ser Ala Pro Pro Pro Ser Gly Ser Gly Thr Ser Lys Ile<br>505 510 515 | 1592 | |
| GAC AAA TAT GCC CGT ATT CTC TTT CCA GTC ACA TTT GGG GCA TTT AAC<br>Asp Lys Tyr Ala Arg Ile Leu Phe Pro Val Thr Phe Gly Ala Phe Asn<br>520 525 530 | 1640 | |
| ATG GTT TAT TGG GTT GTT TAT TTA TCT AAG GAC ACT ATG GAG AAA TCA<br>Met Val Tyr Trp Val Val Tyr Leu Ser Lys Asp Thr Met Glu Lys Ser<br>535 540 545 550 | 1688 | |

```
GAA AGT CTA ATG TGAATTC                                              1707
Glu Ser Leu Met
```

(2) INFORMATION FOR SEQ ID NO: 8:

(i) SEQUENCE CHARACTERISTICS:
        (A) LENGTH: 554 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

```
Met Val Ser Ala Lys Lys Val Pro Ala Ile Thr Leu Ser Ala Gly Val
 1               5                  10                  15

Ser Phe Ala Leu Leu Arg Phe Leu Cys Leu Ala Val Cys Leu Asn Glu
                20                  25                  30

Ser Pro Gly Gln Asn Gln Lys Glu Glu Lys Leu Cys Thr Glu Asn Phe
            35                  40                  45

Thr Arg Ile Leu Asp Ser Leu Leu Asp Gly Tyr Asp Asn Arg Leu Arg
50                  55                  60

Pro Gly Phe Gly Gly Pro Val Thr Glu Val Lys Thr Asp Ile Tyr Val
65                  70                  75                  80

Thr Ser Phe Gly Pro Val Ser Asp Val Glu Val Glu Tyr Thr Met Asp
                85                  90                  95

Val Phe Phe Arg Gln Thr Trp Ile Asp Lys Arg Leu Lys Tyr Asp Gly
                100                 105                 110

Pro Ile Glu Ile Leu Arg Leu Asn Asn Met Met Val Thr Lys Val Trp
            115                 120                 125

Thr Pro Asp Thr Phe Phe Arg Asn Gly Lys Lys Ser Val Ser His Asn
130                 135                 140

Met Thr Ala Pro Asn Lys Leu Phe Arg Ile Met Arg Asn Gly Thr Ile
145                 150                 155                 160

Leu Tyr Thr Met Arg Leu Thr Ile Ser Ala Glu Cys Pro Met Arg Leu
                165                 170                 175

Val Asp Phe Pro Met Asp Gly His Ala Cys Pro Val Lys Phe Gly Ser
                180                 185                 190

Tyr Ala Tyr Pro Lys Ser Glu Met Ile Tyr Thr Trp Thr Lys Gly Pro
            195                 200                 205

Glu Lys Ser Val Glu Val Pro Lys Glu Ser Ser Leu Val Gln Tyr
            210                 215                 220

Asp Leu Ile Gly Gln Thr Val Ser Ser Glu Thr Ile Lys Ser Ile Thr
225                 230                 235                 240

Gly Glu Tyr Ile Val Met Thr Val Tyr Phe His Leu Arg Arg Lys Met
                245                 250                 255

Gly Tyr Phe Met Ile Gln Thr Tyr Ile Pro Cys Ile Met Thr Val Ile
                260                 265                 270

Leu Ser Gln Val Ser Phe Trp Ile Asn Lys Glu Ser Val Pro Ala Arg
            275                 280                 285

Thr Val Phe Gly Ile Thr Thr Val Leu Thr Met Thr Thr Leu Ser Ile
            290                 295                 300

Ser Ala Arg His Ser Leu Pro Lys Val Ser Tyr Ala Thr Ala Met Asp
305                 310                 315                 320

Trp Phe Ile Ala Val Cys Phe Ala Phe Val Phe Ser Ala Leu Ile Glu
                325                 330                 335
```

```
Phe Ala Ala Val Asn Tyr Phe Thr Asn Ile Gln Met Glu Lys Ala Lys
                340                 345                 350

Arg Lys Thr Ser Lys Pro Pro Gln Glu Val Pro Ala Ala Pro Val Gln
            355                 360                 365

Arg Glu Lys His Pro Glu Ala Pro Leu Gln Asn Thr Asn Ala Asn Leu
        370                 375                 380

Asn Met Arg Lys Arg Thr Asn Ala Leu Val His Ser Glu Ser Asp Val
385                 390                 395                 400

Gly Asn Arg Thr Glu Val Gly Asn His Ser Ser Lys Ser Ser Thr Val
                405                 410                 415

Val Gln Glu Ser Ser Lys Gly Thr Pro Arg Ser Tyr Leu Ala Ser Ser
            420                 425                 430

Pro Asn Pro Phe Ser Arg Ala Asn Ala Ala Glu Thr Ile Ser Ala Ala
        435                 440                 445

Arg Ala Leu Pro Ser Ala Ser Pro Thr Ser Ile Arg Thr Gly Tyr Met
450                 455                 460

Pro Arg Lys Ala Ser Val Gly Ser Ala Ser Thr Arg His Val Phe Gly
465                 470                 475                 480

Ser Arg Leu Gln Arg Ile Lys Thr Thr Val Asn Thr Ile Gly Ala Thr
                485                 490                 495

Gly Lys Leu Ser Ala Thr Pro Pro Ser Ala Pro Pro Ser Gly
            500                 505                 510

Ser Gly Thr Ser Lys Ile Asp Lys Tyr Ala Arg Ile Leu Phe Pro Val
                515                 520                 525

Thr Phe Gly Ala Phe Asn Met Val Tyr Trp Val Val Tyr Leu Ser Lys
            530                 535                 540

Asp Thr Met Glu Lys Ser Glu Ser Leu Met
545                 550

(2) INFORMATION FOR SEQ ID NO: 9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

AGCCCGAATT CCATGGACGT TCTGGGCTGG CTG                                33

(2) INFORMATION FOR SEQ ID NO: 10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GGTTTCCAAG CTTACTTTGG AGAGGTAGC                                    29

(2) INFORMATION FOR SEQ ID NO: 11:

(i) SEQUENCE CHARACTERISTICS:
        (A) LENGTH: 1555 base pairs
        (B) TYPE: nucleic acid
        (C) STRANDEDNESS: single
```

(D) TOPOLOGY: linear (ii) MOLECULE TYPE: cDNA (ix) FEATURE:
        (A) NAME/KEY: Coding Sequence
        (B) LOCATION: 47...1402
        (D) OTHER INFORMATION:

(xi) SEQUENCE DESCRIPTION: SEQ ID NO: 11:

```
GAATTCCCCA AGTTTGCGCG GACCCCGTCC CGAGCCCGCC GCGGCC ATG GAC GCG            55
                                                 Met Asp Ala
                                                  1

CCC GCC CGG CTG CTG GCC CCG CTC CTG CTC CTC TGC GCG CAG CAG CTC          103
Pro Ala Arg Leu Leu Ala Pro Leu Leu Leu Leu Cys Ala Gln Gln Leu
     5                  10                  15

CGC GGC ACC AGA GCG ATG AAT GAC ATC GGC GAC TAC GTG GGC TCC AAC          151
Arg Gly Thr Arg Ala Met Asn Asp Ile Gly Asp Tyr Val Gly Ser Asn
 20                  25                  30                  35

CTG GAG ATC TCC TGG CTC CCC AAC CTG GAC GGG CTG ATA GCC GGT TAC          199
Leu Glu Ile Ser Trp Leu Pro Asn Leu Asp Gly Leu Ile Ala Gly Tyr
                 40                  45                  50

GCC CGC AAC TTC CGG CCT GGC ATC GGA GGC CCC CCC GTG AAT GTG GCC          247
Ala Arg Asn Phe Arg Pro Gly Ile Gly Gly Pro Pro Val Asn Val Ala
             55                  60                  65

CTT GCC CTG GAG GTG GCC AGC ATC GAC CAC ATC TCA GAG GCC AAC ATG          295
Leu Ala Leu Glu Val Ala Ser Ile Asp His Ile Ser Glu Ala Asn Met
         70                  75                  80

GAG TAC ACC ATG ACG GTG TTC CTG CAC CAG AGC TGG CGG GAC AGC AGG          343
Glu Tyr Thr Met Thr Val Phe Leu His Gln Ser Trp Arg Asp Ser Arg
     85                  90                  95

CTC TCC TAC AAC CAC ACC AAC GAG ACC CTG GGC CTG GAC AGC CGC TTC          391
Leu Ser Tyr Asn His Thr Asn Glu Thr Leu Gly Leu Asp Ser Arg Phe
100                 105                 110                 115

GTG GAC AAG CTG TGG CTG CCC GAC ACC TTC ATC GTG AAC GCC AAG TCG          439
Val Asp Lys Leu Trp Leu Pro Asp Thr Phe Ile Val Asn Ala Lys Ser
                120                 125                 130

GCC TGG TTC CAC GAC GTG ACG GTG GAG AAC AAG CTC ATC CGG CTG CAG          487
Ala Trp Phe His Asp Val Thr Val Glu Asn Lys Leu Ile Arg Leu Gln
            135                 140                 145

CCC GAC GGG GTG ATC CTG TAC AGC ATC CGA ATC ACC TCC ACT GTG GCC          535
Pro Asp Gly Val Ile Leu Tyr Ser Ile Arg Ile Thr Ser Thr Val Ala
        150                 155                 160

TGC GAC ATG GAC CTG GCC AAA TTC CCC ATG GAC GAG CAG GAG TGC ATG          583
Cys Asp Met Asp Leu Ala Lys Phe Pro Met Asp Glu Gln Glu Cys Met
    165                 170                 175

CTG GAC CTG GAG AGC TAC GGT TAC TCA TCG GAG GAC ATC GTC TAC TAC          631
Leu Asp Leu Glu Ser Tyr Gly Tyr Ser Ser Glu Asp Ile Val Tyr Tyr
180                 185                 190                 195

TGG TCG GAG AGC CAG GAG CAC ATC CAC GGG CTG GAC AAG CTG CAG CTG          679
Trp Ser Glu Ser Gln Glu His Ile His Gly Leu Asp Lys Leu Gln Leu
                200                 205                 210

GCG CAG TTC ACC ATC ACC AGC TAC CGC TTC ACC ACG GAG CTG ATG AAC          727
Ala Gln Phe Thr Ile Thr Ser Tyr Arg Phe Thr Thr Glu Leu Met Asn
            215                 220                 225

TTC AAG TCC GCT GGC CAG TTC CCA CGG CTC AGC CTG CAC TTC CAC CTG          775
Phe Lys Ser Ala Gly Gln Phe Pro Arg Leu Ser Leu His Phe His Leu
        230                 235                 240

CGG AGG AAC CGC GGC GTG TAC ATC ATC CAA TCC TAC ATG CCC TCC GTC          823
Arg Arg Asn Arg Gly Val Tyr Ile Ile Gln Ser Tyr Met Pro Ser Val
    245                 250                 255
```

```
CTG CTG GTC GCC ATG TCC TGG GTC TCC TTC TGG ATC AGC CAG GCG GCG      871
Leu Leu Val Ala Met Ser Trp Val Ser Phe Trp Ile Ser Gln Ala Ala
260                 265                 270                 275

GTG CCC GCC AGG GTG TCT CTA GGC ATC ACC ACG GTG CTG ACG ATG ACC      919
Val Pro Ala Arg Val Ser Leu Gly Ile Thr Thr Val Leu Thr Met Thr
                280                 285                 290

ACG CTC ATG GTC AGT GCC CGC TCC TCC CTG CCA CGG GCA TCA GCC ATC      967
Thr Leu Met Val Ser Ala Arg Ser Ser Leu Pro Arg Ala Ser Ala Ile
            295                 300                 305

AAG GCA CTG GAC GTC TAC TTC TGG ATC TGC TAT GTC TTC GTG TTT GCC     1015
Lys Ala Leu Asp Val Tyr Phe Trp Ile Cys Tyr Val Phe Val Phe Ala
        310                 315                 320

GCC CTG GTG GAG TAC GCC TTT GCT CAT TTC AAC GCC GAC TAC AGG AAG     1063
Ala Leu Val Glu Tyr Ala Phe Ala His Phe Asn Ala Asp Tyr Arg Lys
    325                 330                 335

AAG CAG AAG GCC AAG GTC AAG GTC TCC AGG CCG AGG GCA GAG ATG GAC     1111
Lys Gln Lys Ala Lys Val Lys Val Ser Arg Pro Arg Ala Glu Met Asp
340                 345                 350                 355

GTG AGG AAC GCC ATT GTC CTC TTC TCC CTC TCT GCT GCC GGC GTC ACG     1159
Val Arg Asn Ala Ile Val Leu Phe Ser Leu Ser Ala Ala Gly Val Thr
                360                 365                 370

CAG GAG CTG GCC ATC TCC CGC CGG CAG CGC CGC GTC CCG GGG AAC CTG     1207
Gln Glu Leu Ala Ile Ser Arg Arg Gln Arg Arg Val Pro Gly Asn Leu
            375                 380                 385

ATG GGC TCC TAC AGG TCG GTG GGG GTG GAG ACA GGG GAG ACG AAG AAG     1255
Met Gly Ser Tyr Arg Ser Val Gly Val Glu Thr Gly Glu Thr Lys Lys
        390                 395                 400

GAG GGG GCA GCC CGC TCA GGA GGC CAG GGG GGC ATC CGT GCC CGG CTC     1303
Glu Gly Ala Ala Arg Ser Gly Gly Gln Gly Gly Ile Arg Ala Arg Leu
    405                 410                 415

AGG CCC ATC GAC GCA GAC ACC ATT GAC ATT TAC GCC CGC GCT GTG TTC     1351
Arg Pro Ile Asp Ala Asp Thr Ile Asp Ile Tyr Ala Arg Ala Val Phe
420                 425                 430                 435

CCT GCG GCG TTT GCG GCC GTC AAT GTC ATC TAC TGG GCG GCA TAC GCC     1399
Pro Ala Ala Phe Ala Ala Val Asn Val Ile Tyr Trp Ala Ala Tyr Ala
                440                 445                 450

ATG TGAGCACAGG ACTCAGGCCA CCCTCGCTTG TCCTGGCGCC CGGCGGCAGC          1452
Met

TGCCCAGAAA CTTCCTGGGA GAAAGAGCCC TCGGGCTGCC TTCCCCTCTG CGTGTTTCGA   1512

AGTGGGATGA CAGTCGGCCA CGGAAAACAA GAGGAAGCCT CGG                     1555

(2) INFORMATION FOR SEQ ID NO: 12:

(i) SEQUENCE CHARACTERISTICS:
        (A) LENGTH: 452 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

Met Asp Ala Pro Ala Arg Leu Leu Ala Pro Leu Leu Leu Leu Cys Ala
1               5                   10                  15

Gln Gln Leu Arg Gly Thr Arg Ala Met Asn Asp Ile Gly Asp Tyr Val
            20                  25                  30

Gly Ser Asn Leu Glu Ile Ser Trp Leu Pro Asn Leu Asp Gly Leu Ile
        35                  40                  45

Ala Gly Tyr Ala Arg Asn Phe Arg Pro Gly Ile Gly Pro Pro Val
    50                  55                  60
```

Asn Val Ala Leu Ala Leu Glu Val Ala Ser Ile Asp His Ile Ser Glu
65                  70                  75                  80

Ala Asn Met Glu Tyr Thr Met Thr Val Phe Leu His Gln Ser Trp Arg
                85                  90                  95

Asp Ser Arg Leu Ser Tyr Asn His Thr Asn Glu Thr Leu Gly Leu Asp
            100                 105                 110

Ser Arg Phe Val Asp Lys Leu Trp Leu Pro Asp Thr Phe Ile Val Asn
        115                 120                 125

Ala Lys Ser Ala Trp Phe His Asp Val Thr Val Glu Asn Lys Leu Ile
130                 135                 140

Arg Leu Gln Pro Asp Gly Val Ile Leu Tyr Ser Ile Arg Ile Thr Ser
145                 150                 155                 160

Thr Val Ala Cys Asp Met Asp Leu Ala Lys Phe Pro Met Asp Glu Gln
            165                 170                 175

Glu Cys Met Leu Asp Leu Glu Ser Tyr Gly Tyr Ser Ser Glu Asp Ile
            180                 185                 190

Val Tyr Tyr Trp Ser Glu Ser Gln Glu His Ile His Gly Leu Asp Lys
            195                 200                 205

Leu Gln Leu Ala Gln Phe Thr Ile Thr Ser Tyr Arg Phe Thr Thr Glu
210                 215                 220

Leu Met Asn Phe Lys Ser Ala Gly Gln Phe Pro Arg Leu Ser Leu His
225                 230                 235                 240

Phe His Leu Arg Arg Asn Arg Gly Val Tyr Ile Ile Gln Ser Tyr Met
            245                 250                 255

Pro Ser Val Leu Leu Val Ala Met Ser Trp Val Ser Phe Trp Ile Ser
            260                 265                 270

Gln Ala Ala Val Pro Ala Arg Val Ser Leu Gly Ile Thr Thr Val Leu
            275                 280                 285

Thr Met Thr Thr Leu Met Val Ser Ala Arg Ser Ser Leu Pro Arg Ala
290                 295                 300

Ser Ala Ile Lys Ala Leu Asp Val Tyr Phe Trp Ile Cys Tyr Val Phe
305                 310                 315                 320

Val Phe Ala Ala Leu Val Glu Tyr Ala Phe Ala His Phe Asn Ala Asp
            325                 330                 335

Tyr Arg Lys Lys Gln Lys Ala Lys Val Lys Val Ser Arg Pro Arg Ala
            340                 345                 350

Glu Met Asp Val Arg Asn Ala Ile Val Leu Phe Ser Leu Ser Ala Ala
            355                 360                 365

Gly Val Thr Gln Glu Leu Ala Ile Ser Arg Arg Gln Arg Arg Val Pro
370                 375                 380

Gly Asn Leu Met Gly Ser Tyr Arg Ser Val Gly Val Glu Thr Gly Glu
385                 390                 395                 400

Thr Lys Lys Glu Gly Ala Ala Arg Ser Gly Gln Gly Gly Ile Arg
            405                 410                 415

Ala Arg Leu Arg Pro Ile Asp Ala Asp Thr Ile Asp Ile Tyr Ala Arg
            420                 425                 430

Ala Val Phe Pro Ala Ala Phe Ala Ala Val Asn Val Ile Tyr Trp Ala
            435                 440                 445

Ala Tyr Ala Met
450

(2) INFORMATION FOR SEQ ID NO: 13:

-continued

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

TAATGAGTTT AAACCATAGC TTCTTCCAGT                                              30

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

CATGATGGAT CCGCCCGCTC AGAC                                                    24
```